(12) United States Patent
Hiller et al.

(10) Patent No.: US 7,958,793 B2
(45) Date of Patent: Jun. 14, 2011

(54) SAMPLE SYSTEM FOR FLUID SAMPLES

(75) Inventors: Julia Hiller, Nuremberg (DE);
Karl-Heinz Zacher, Buch am Buchrain (DE); Dirk Weuster-Botz, Dachau (DE); Andreas Kusterer, Poing (DE)

(73) Assignee: Technische Universität München, Munich (DE)

( * ) Notice: Subject to any disclaimer, the term of this patent is extended or adjusted under 35 U.S.C. 154(b) by 350 days.

(21) Appl. No.: 12/089,829

(22) PCT Filed: Oct. 13, 2006

(86) PCT No.: PCT/EP2006/009928
§ 371 (c)(1),
(2), (4) Date: Jun. 25, 2008

(87) PCT Pub. No.: WO2007/042323
PCT Pub. Date: Apr. 19, 2007

(65) Prior Publication Data
US 2009/0038419 A1 Feb. 12, 2009

(30) Foreign Application Priority Data
Oct. 14, 2005 (DE) .......................... 10 2005 049 226

(51) Int. Cl.
*G01N 1/10* (2006.01)
(52) U.S. Cl. .................................................. 73/864.73
(58) Field of Classification Search ............... 73/863.81, 73/863.85, 863.86, 864.74, 864.73
See application file for complete search history.

(56) References Cited

U.S. PATENT DOCUMENTS

| | | | |
|---|---|---|---|
| 3,469,572 A | 9/1969 | Nehring | 604/66 |
| 4,669,321 A | 6/1987 | Meyer | 73/863.85 |
| 4,887,472 A * | 12/1989 | Jansen | 73/863.86 |
| 5,301,560 A | 4/1994 | Anderson et al. | 73/863.86 |
| 5,313,969 A | 5/1994 | Hsieh | 600/577 |
| 5,907,110 A | 5/1999 | Garcia et al. | 73/864.74 |

FOREIGN PATENT DOCUMENTS
EP      0319072 B1   7/2008
WO  2004/087859 A2  10/2004

OTHER PUBLICATIONS

Uwe Theobald, Werner Mailinger, Matthias Reuss, and Manfred Rizzi, in Vivo analysis of Glucose-Induced Fast Changes in Yeast Adenine Nucleotide Pool Applying a Rapid Sampling Technique, Analytical Biochemistry 214, 31-37 (1993).

* cited by examiner

*Primary Examiner* — Hezron Williams
*Assistant Examiner* — Tamiko D Bellamy
(74) *Attorney, Agent, or Firm* — Young Basile

(57) ABSTRACT

Disclosed herein are embodiments of a sampling system for fluid samples having sample receiving vessel for receiving the sample, which is sealed by a septum and holder for the sample receiving vessel for receiving and holding the sample receiving vessel and also a sample probe for dipping into a fluid volume and for taking a fluid sample from the fluid volume, the sample probe being configured as a hollow volume which, at one end, has a first opening for introducing the holder and the sample receiving vessel and, at another end, is sealed by a first valve which is provided with a hollow needle which projects into the interior of the sample probe said valve being able to be opened by contact with at least one of the group comprising the holder and the sample receiving vessel and then connecting the exterior of the sample probe to the inner volume of the hollow needle.

18 Claims, 13 Drawing Sheets

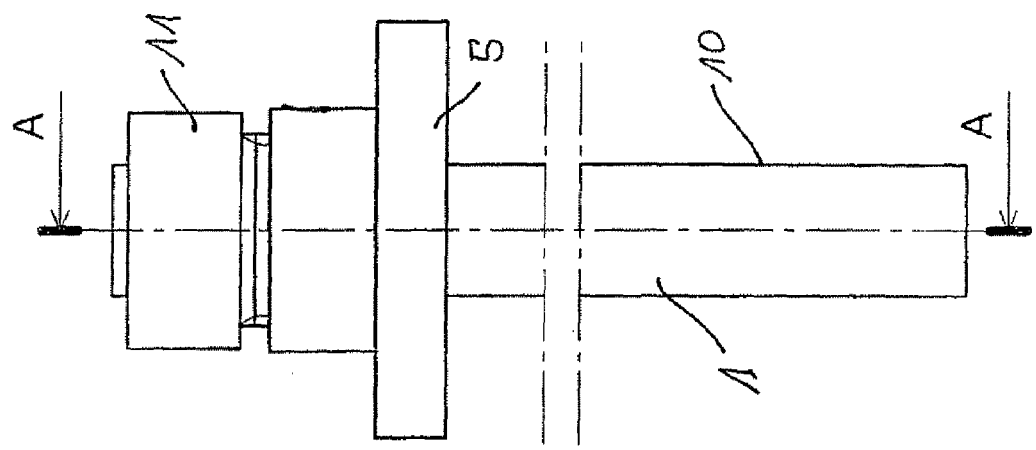
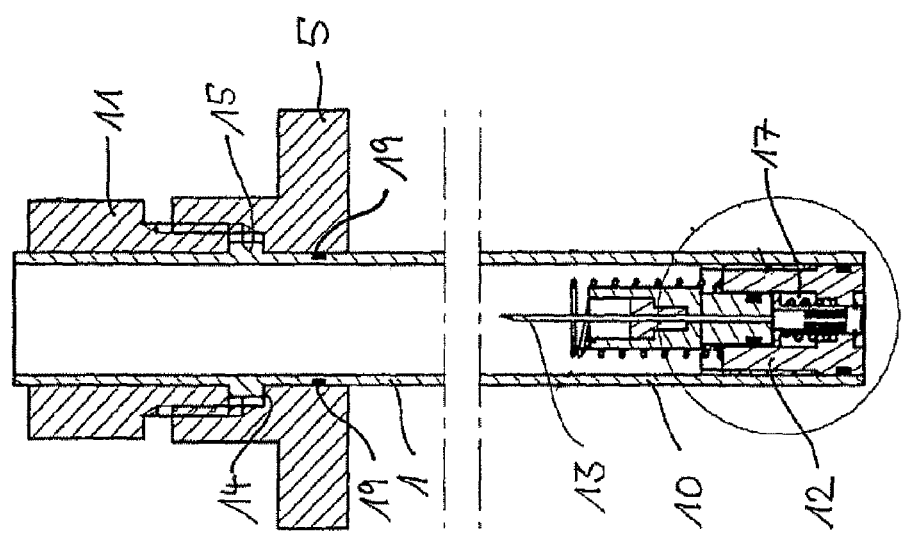

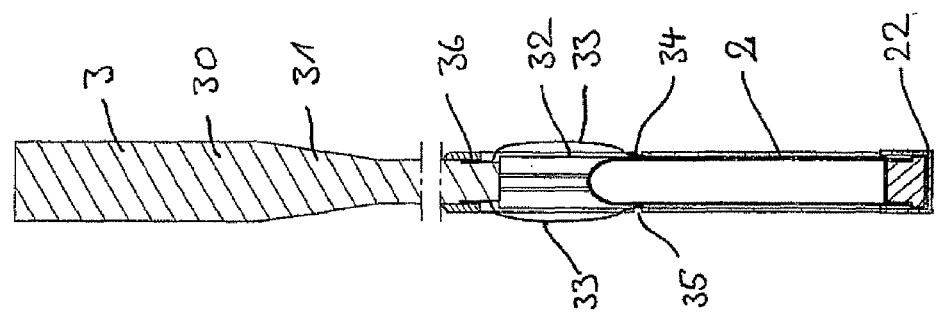
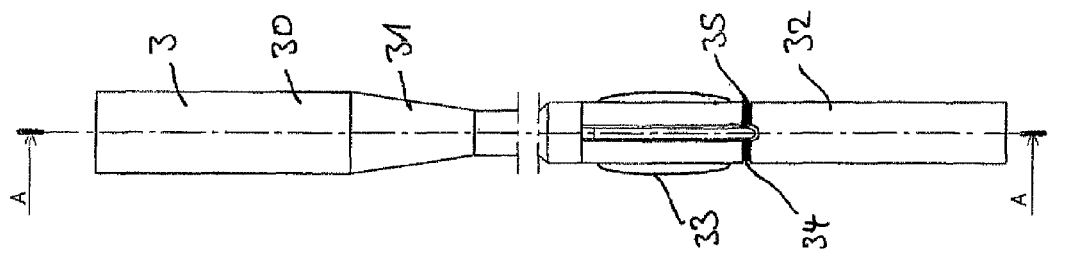
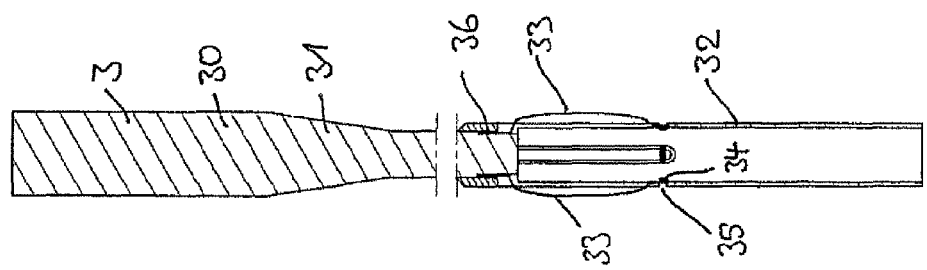
Fig. 6

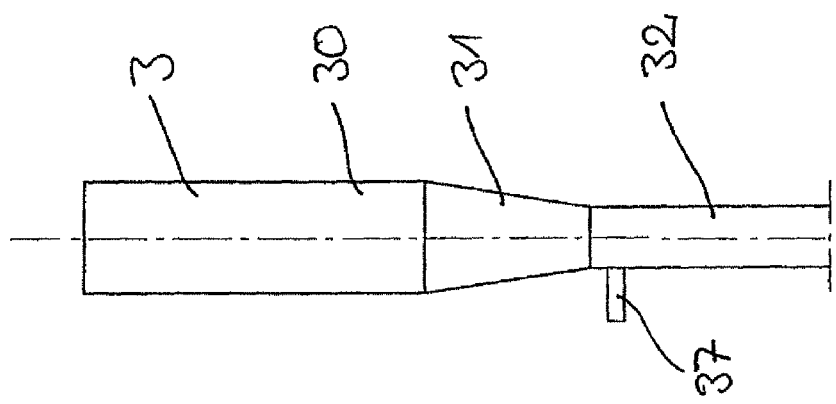
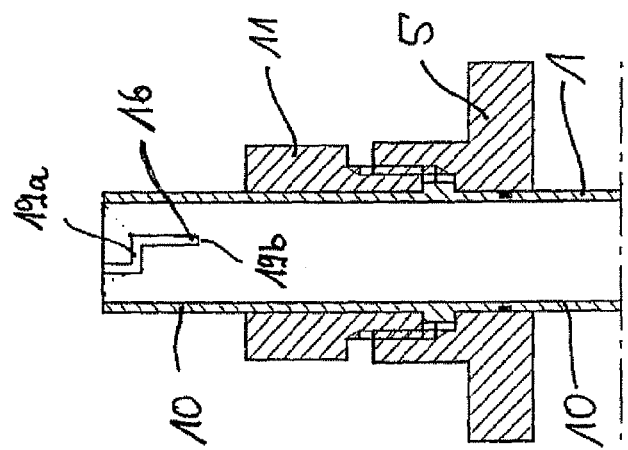
Fig. 7

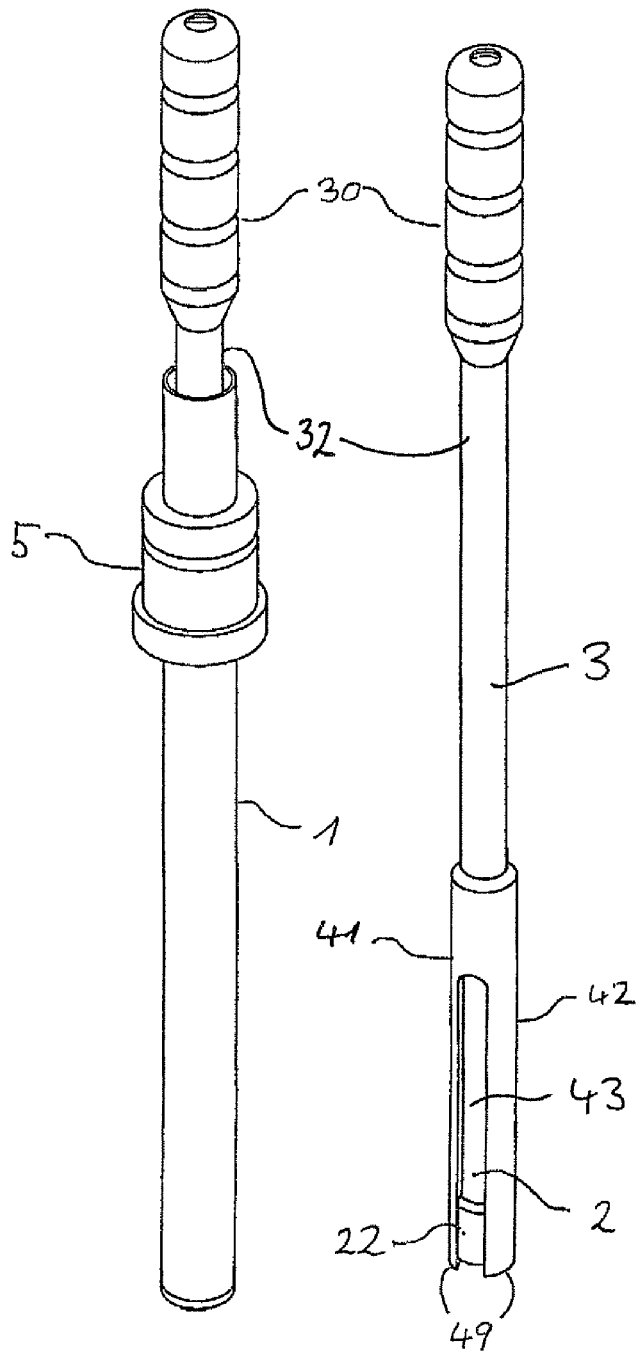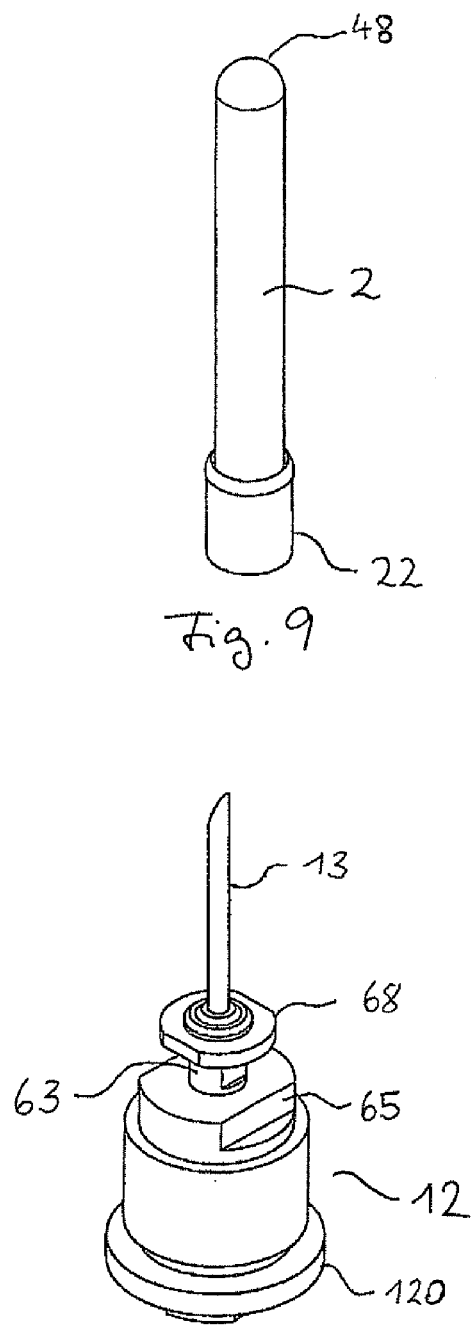

SAMPLE SYSTEM FOR FLUID SAMPLES

BACKGROUND OF THE INVENTION

The present invention relates to a sampling system for fluid samples. Sampling systems of this type are required in particular if a sample is intended to be taken from a liquid or a gas volume. Sampling systems of this type are required in particular in order to monitor the process in bioreactors, i.e. in particular in the field of biotechnology, but also in the chemical industry, pharmaceutical industry, foodstuffs industry and also in the field of environmental technology and for official bodies, for example environmental protection agencies or analysis laboratories.

In the case of laboratory bioreactors made of stainless steel, normally cocks and valves in the base of the laboratory bioreactor are used for manual sampling. In the case of glass reactors which are used frequently on a laboratory scale and are accessible only from the top, manual sampling is normally implemented with the help of a so-called dip pipe. The sample is hereby conveyed out of the bioreactor via a tube with a syringe and using a pump. This mode of operation has the result that the sample is normally drawn out of the reactor from the top via a dip pipe. If the sample is drawn merely from the surface of the reactor volume, then inaccurate samples can be produced. However, if the dip pipe extends very far into the volume, then a relative large dead volume is produced, which can likewise effect inaccuracy of the sample or entails a large sample loss since the dead volume usually must then be discarded.

It is therefore the object of the present invention to make available a reliable sampling system which enables manual sampling with a low dead volume.

This object is achieved by the sampling system as disclosed hereinafter. Advantageous developments of the sampling system according to the invention are also revealed.

SUMMARY

According to the invention, the sampling system which can use all samples, in particular for gases and liquids, has three individual elements which are however coordinated to each other. As the first element, a sample probe is inserted into the bioreactor which can be configured as a hollow volume, in particular as a hollow tube. This sample probe is open at one end thereof and sealed at the other end thereof, which protrudes into the reactor, via a valve. The valve has a hollow needle, via which the outer side of the valve is connected to the inner side of the valve when the valve is open.

Furthermore, a sample receiving vessel is provided which serves to receive the withdrawn sample. This is sealed with a septum and dimensioned such that it can be introduced into the sample probe. If it is introduced sufficiently far into the sample probe, then the septum which is situated at one end thereof is pierced by the hollow needle. Upon further introduction into the sample probe, the sample receiving vessel presses against the valve and thus opens the valve mechanically. The precise mechanism for opening the valve is described later. In this way, an opening between the outer side of the sample probe and the inner volume of the sample receiving vessel is exposed. If the sample receiving vessel is at least partially evacuated, the sample is now suctioned out of the fluid volume to be sampled via the valve and the hollow needle into the inner volume of the sample receiving vessel.

As third element, a holder is provided for the sample receiving vessel, into which holder the sample receiving vessel can be introduced. By means of this holder, a defined introduction of the sample receiving vessel into the sample probe is possible.

The sampling system according to the invention makes it possible to take samples from a fluid volume reproducibly and reliably. It can be used safely and by trained personnel in a simple manner.

Since conventional standardised sample receiving vessels, for example so-called vacutainers of the company BD GmbH, can be used as sample receiving vessel, the current costs for the sampling system according to the invention can be kept low. In particular the costs for the used articles, such as sample receiving vessels, can be kept reasonable due to the use of standard commercial products.

The sampling system according to the invention has the advantage in addition that the dead volume, namely the through-volume of the valve and of the hollow needle, is small. However, removal from a reactor, in particular even from a glass reactor, is possible via the sample probe.

The system can therefore be used with any type of bioreactors, in particular even with small or medium-sized glass laboratory reactors. As a result of the constantly ensured seal of the sample to be withdrawn and of the fluid to be sampled from the exterior, sampling of toxic or health-endangering materials is also possible without further protective precautions or with low protective precautions.

The sample receiving vessel can be filled in addition with reagents in order to prevent for example undesired reactions in the sample after the sampling.

It is possible in addition to fill a sample receiving vessel with a sterilising solution and to introduce this sample receiving vessel into the sample probe, after or before a sample is taken. As a result, it is possible to keep the hollow needle sterile immediately after the sampling, before sampling or during the entire time between two samplings.

The sample probe is advantageously a stainless steel tube which is open at the top and is sealed at the lower end thereof with the valve. Its external diameter should be chosen such that it can be introduced into the standard connection piece of a laboratory reactor. The sample probe can in addition have a spring which is compressed when introducing the sample receiving vessel by the latter so that a force is exerted on the sample receiving vessel which pushes the latter out of the sample probe again after completion of the sampling. As a result, the removal of the sample receiving vessel from the sample probe is assisted in addition.

The holder for the sample receiving vessel can be configured as a hollow tube, the internal diameter of which is the same or slightly larger than the external diameter of the sample receiving vessel. This must apply at least for a part of the sample receiving vessel since it is merely required to introduce the sample receiving vessel partially into the holder. The holder can have in addition advantageously a gripping element in order to enable simple operation. This can abut in the longitudinal direction against the hollow tube, the diameter of the gripping element being able also to be larger or smaller than the external diameter of the hollow tube. In the latter case, a conical transition between the hollow tube and the gripping element is then advantageous.

The holder can in addition have spring elements which fix the sample receiving vessel in the holder. This can be effected for example via leaf springs which are disposed on the outer side of the hollow tube and, with their free end or with a free region, press on an introduced sample receiving vessel through an opening in the hollow tube. In this case, the leaf springs are further compressed and the sample receiving vessel is held even more firmly when the holder is introduced into the sample probe. Between the regions of the leaf springs, which press on the sample receiving vessel, and the sample receiving vessel itself, an O-ring can be situated, which is situated on the inner side of the hollow tube of the holder or is inserted in a circumferential groove in the wall of the hollow tube of the holder. In addition, this improves the retaining force and reduces the risk of damage to the sample receiving vessel by the resilient elements.

In a further advantageous embodiment, the holder has a bolt or a pin which protrudes outwards. A corresponding groove is inserted in the sample probe for this pin so that the holder with the pin can be introduced into the sample probe in such a manner that the pin slides in the groove. The groove can have a first step similar to a bayonet closure in which further introduction of the holder into the sample probe is possible only after rotation of the holder. In addition, it can have an end stop which fixes the position of the holder in the sample probe, in which the holder is introduced to the maximum into the sample probe.

The first step of the groove can be designed now such that the holder with the pin is introduced only so far into the sample probe that the septum which seals the sample receiving vessel is pierced just by the needle of the valve but the valve is still closed. This position is suitable in particular for sterilising the hollow needle with a sample receiving vessel which contains a sterilising agent or for keeping it sterile in this position.

After rotating the holder and further introduction of the holder into the sample probe, the holder or the sample receiving vessel then exerts a force on the valve so that the valve is opened and now a sample is drawn into the sample receiving vessel via the valve and the hollow needle. This is the position of the holder in which sampling is effected.

According to the invention, it is of course also possible to dispose the corresponding groove on the outer side of the holder and to provide the sample probe with an inwardly protruding pin. The same effect is therefore achieved as by a pin on the holder and a stepped groove on the sample probe.

BRIEF DESCRIPTIONS OF THE DRAWINGS

Examples of sampling systems according to the invention are now given in the following. There are shown FIG. 1 a sampling system in a bioreactor;

FIG. 2 a sampling probe in section (FIG. 2A) and in front view (FIG. 2B), FIG. 2A representing a section along the line A-A in FIG. 2B;

FIG. 3 an enlarged view of the end of the sampling probe of FIG. 2, closed with a valve;

FIG. 4 a sample receiving vessel;

FIG. 5 a sample receiving vessel in various positions within a sample probe;

FIG. 6 three different views or positions of a holder;

FIG. 7 a further example of a sampling system according to the invention.

FIG. 8 shows a sampling system according to the invention in which the sample vessel is retained in a retaining clip.

FIG. 9 shows a sampling vessel.

FIG. 11 shows a valve according to the invention with a canula.

DETAILED DESCRIPTION

Figure 1:
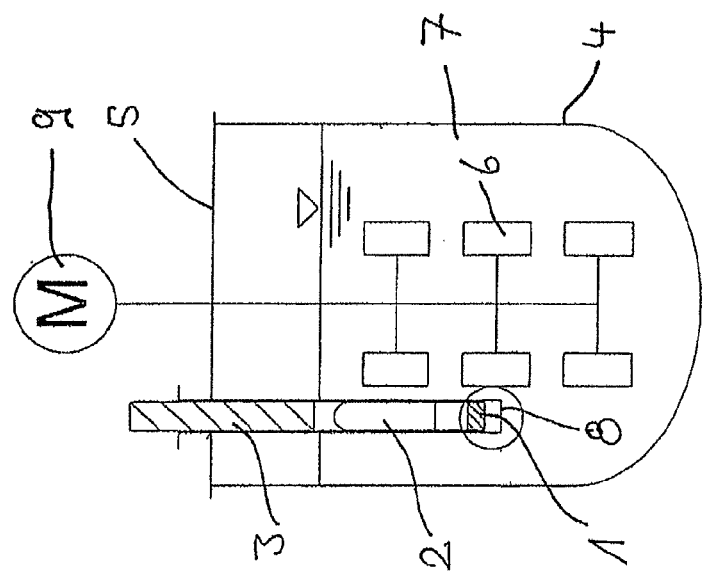

FIG. 1 shows the construction and mode of operation of a sampling system according to the invention in the example of a laboratory bioreactor 4. In the laboratory bioreactor 4, which is closed by a cover 5, there is situated a cell suspension 7 which is kept in suspension by an agitator 6. A sampling system which comprises in total three elements is now dipped into this cell suspension 7. These are, on the one hand, a sample probe 1 which is inserted into the reactor closure or cover 5. It is dimensioned such that it can be introduced into a standard connection piece 8 of the reactor 4.

The sample probe itself is a stainless steel tube which is open at the top and at the lower end of which a sampling valve is situated.

The sample probe is now dipped into the cell suspension 7 and thus makes possible, at the lower end thereof, a sampling position which is extensively in the interior of the reactor 4. As a result, the sample is removed, on the one hand, directly in the interior of the cell suspension 7 and, on the other hand, transport of the sample from the cell suspension 7 into a sample receiving vessel 2 is minimised. As a result, it can be ensured that, on the one hand, the dwell time during the sampling until reaching the sample receiving vessel 2 is kept short and, on the other hand, the dead volumes of this path are only small.

The agitator 6 is actuated by a motor 9 and keeps the cell suspension moving.

Within the sample probe 1, there is situated the sample receiving vessel 2 and also a holder 3 for the sample receiving vessel 2.

FIG. 2 now shows a sample probe 1 according to the invention with a stainless steel tube 10. FIG. 2B shows a plan view on the arrangement of the sample probe 1 in the reactor closure 5 whilst FIG. 2A represents a section through this arrangement along the line A-A in FIG. 2B. Here as in the following, the same or similar elements are provided with the same or similar reference numbers. The stainless steel tube 10 of the sample probe 1 is recessed in the standard connection piece in the reactor cover 5 and secured with a union nut 11. The stainless steel tube 10 has in addition a flange 5 which is in engagement with a flange 14 in the reactor closure 5. The immersion depth of the stainless steel tube 10 is fixed by these two flanges 14 and 15. In addition, in an externally situated circumferential groove in the stainless steel tube at the height of the reactor closure 5, an O-ring 19 which forms a seal between the closure 9 and the stainless steel tube 10 is disposed.

In the stainless steel tube 10, a valve 12 with a valve body 120 is disposed to form a seal at the lower end of said tube. The valve body 120 has a through hole 17 in the longitudinal direction of the sample probe 1. As can be detected in FIG. 3, in an enlarged representation, a valve cylinder 18 is introduced into this boring 17, said valve cylinder abutting for its part against the walls of the boring 17 to form a seal. This seal is improved in addition by an O-ring 123.

Figure 3:
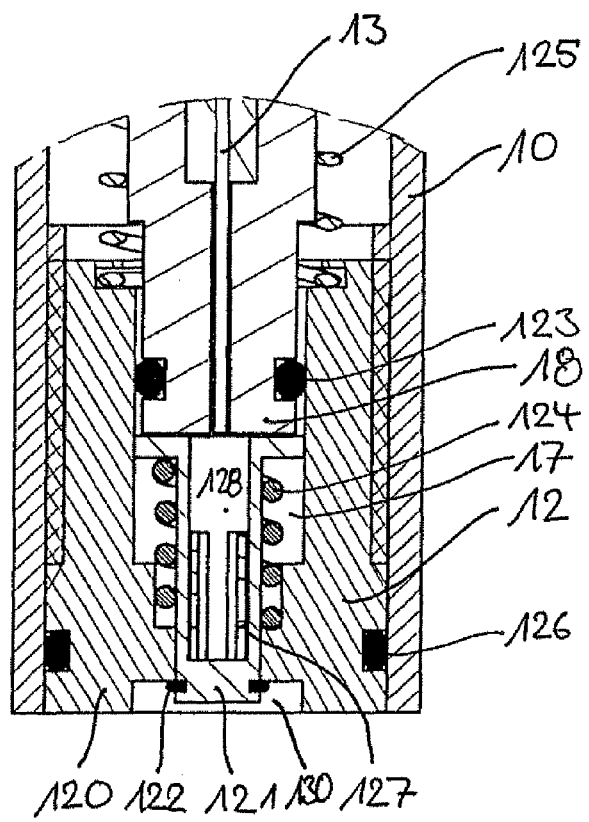

The valve cylinder 18 is mounted resiliently via the spring 124 in the valve body 120 and can be displaced from the position shown in FIG. 3 downwards in opposition to the force of the spring 124 in the longitudinal direction of the sample probe 1.

The valve body 120 has a recess 130 at the end of the sample probe 1, at which recess the valve cylinder 18 protrudes. The valve cylinder 18 is provided there with a circumferential rubber ring seal 122 which seals the gap between the valve cylinder 18 and the valve body 120 when the valve cylinder 18 is displaced by the spring 124 to the maximum into the interior of the sample probe 1.

The valve cylinder 18 has for its part in addition an internal hole 128. Starting from this internal hole 128 there are located in the side walls of the valve cylinder 18 through-openings 127 which connect the outer side of the wall of the valve cylinder 18 to the boring 128.

If the valve cylinder 18 is now pressed downwards in opposition to the spring force of the spring 124, then the borings 127 are exposed and a fluid can flow into the boring 127 and the boring 128 from outwith the sample probe 1.

As can be detected in FIGS. 2 and 3, a hollow needle 13 is disposed in addition in the valve cylinder 18 and communicates with the boring 128 and hence with the inner volume of the valve cylinder 18. This hollow needle 13 is orientated in the longitudinal direction of the sample probe 1 and protrudes by its end orientated away from the valve cylinder 18 beyond the valve cylinder 18.

Figure 4:
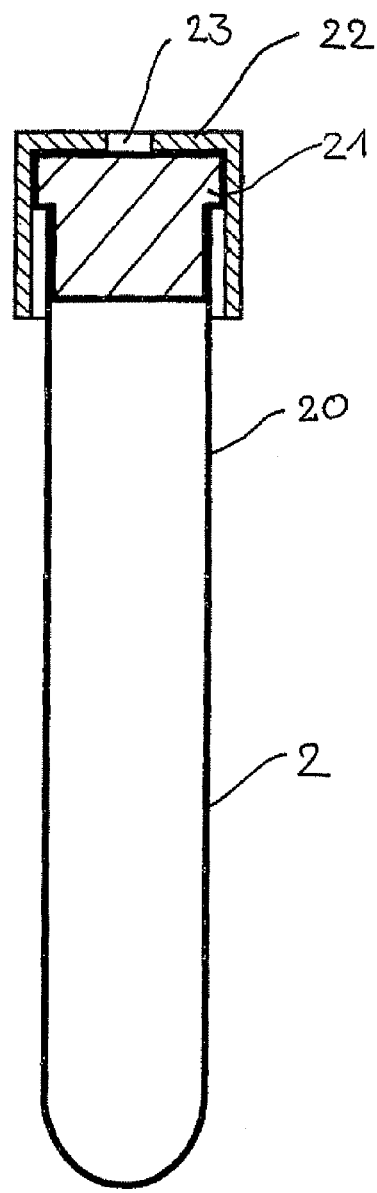

FIG. 4 shows a sample receiving vessel 2 according to the invention. This essentially comprises a test tube 20 made of glass or plastic material, which is closed with a septum 21. Above the septum 21, in the present example made of silicone, a protective cap 22 is disposed in addition which however has an opening 23 in the central axis of the test tube 20. Through this opening 23, the hollow needle 13 can pierce the septum 21 in the application case.

There are suitable in particular as sample receiving vessels 2 conventional so-called "vacutainers" which are already commercially available and are obtainable both empty and filled with different buffers and reagents. They are normally used in the medical field for preparing blood samples. The content of this vessel is therefore also normally already characterised unequivocally by the colour of the protective cap 22 and of the septum 21 and each vessel 2 is already provided with an inscription area.

Vacutainers of this type are obtainable in different volumes and very cheaply. These standardised sample receiving vessels enable use of the present invention in the case of routine checks of processes and plants, for example also by shift personnel or also by official bodies. The analysis which often requires costly and qualified personnel can be affected subsequently in correspondingly qualified and certified laboratories.

The closed construction of the sample receiving vessel 2 is of particular advantage since tampering during sampling and subsequent transport for analysis can be precluded by simple means. Because of the closed construction, also health-endangering or toxic samples can be taken from apparatus, plants or channels without endangering the personnel.

In the non-certified laboratory field, it is also possible to fill with suitable reagents the present sample receiving vessels 2 which are already commercially available, with the help of a syringe, e.g. the vessels 2 can be filled with cold methanol in order immediately to stop biological reactions taking place in the sample during sampling.

Figure 5:
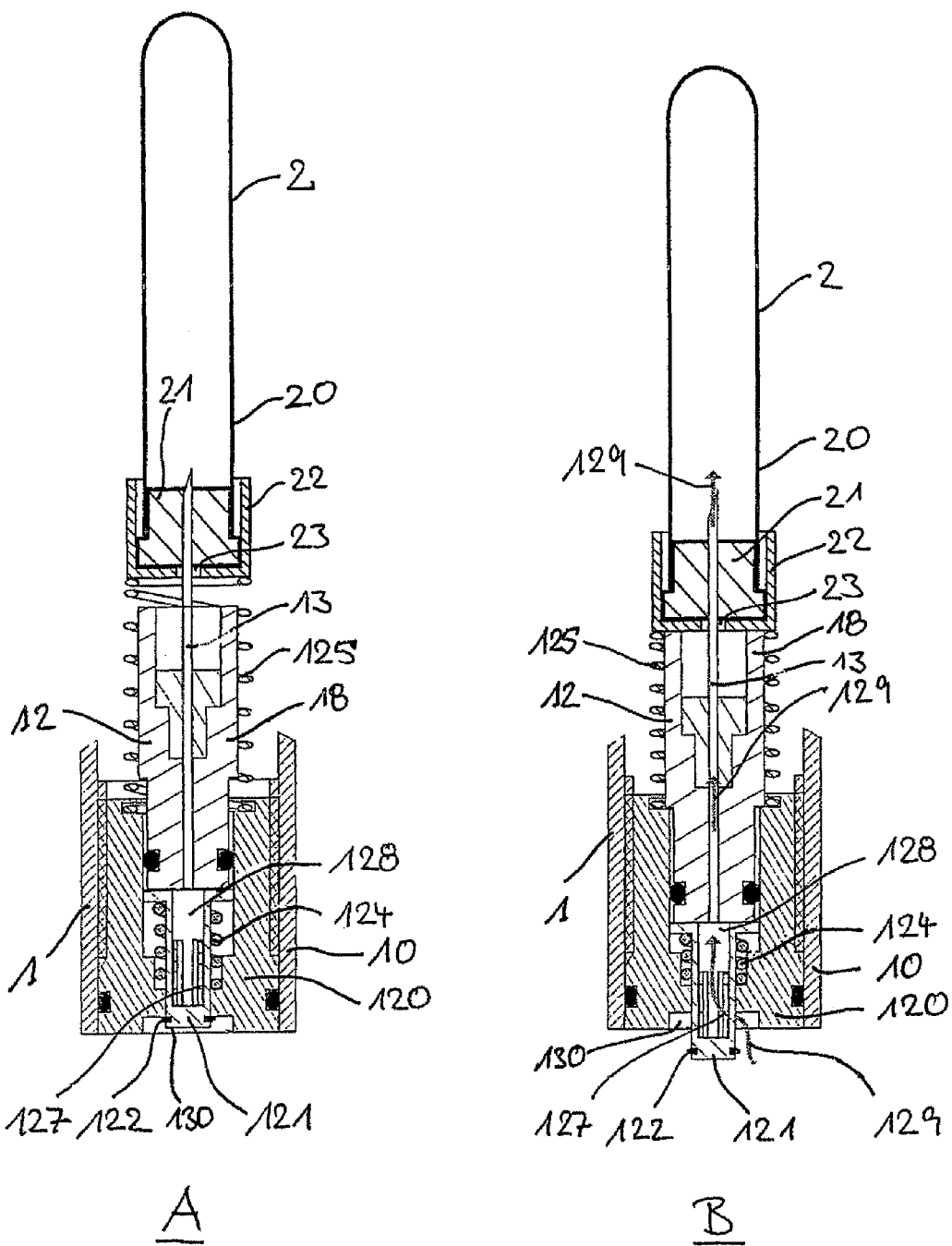

FIG. 5 now shows a sample receiving vessel 2 in two different arrangements relative to the valve 12 of a sample probe 1. In FIG. 5A, a position is thereby represented in which the sample receiving vessel does not yet compress the return spring 125 which surrounds the valve cylinder 18. Since the hollow needle 13 protrudes however sufficiently far out of the valve cylinder 18, it already pierces the septum 21 through the opening 23. In this way, contact between the interior of the hollow needle 13 and the interior of the sample receiving vessel 2 is hence already produced. If the sample receiving vessel 2 is charged with a sterilising solution, then the needle 13 can be sterilised or kept permanently sterile.

The needle 13 for its part can have a cover (not shown here) which normally covers it and which is pressed back when the sample receiving vessel 2 is pressed thereon and hence releases the tip of the hollow needle 13.

FIG. 5B shows a further position in which the protective cap 22 of the sample receiving vessel 2 presses on the valve cylinder 18 and, in this way, presses the foremost part 121 of the valve cylinder 18 out of the recess 130. As a result, the rubber ring 122 is pressed out of its seat and the openings 127 come into contact with the exterior of the sample probe 1. The arrows 129 now show a possible flow path for the fluid to be sampled through the opening 127, the inner volume 128 of the valve cylinder 18 and also the inner volume of the hollow needle 13 into the interior of the sample receiving vessel 2. The spring 125 thereby exerts a restoring force on the sample receiving vessel 2 which however is overcome by the operator during sampling.

Also the spring 124 is compressed by the valve cylinder 18 and thus exerts a restoring force on the valve cylinder 18. With decreasing pressure of the sample receiving vessel 2 on the valve cylinder 18, firstly the valve pin 121 is thus again pushed back into its sealing seat and only thereafter is the sample receiving vessel 2 withdrawn from the hollow needle 13.

FIG. 6 shows a holder of a sampling system according to the invention. This holder 3 is represented in FIG. 6B in plan view and in FIG. 6A in a sectional view along the section A-A in FIG. 6B. The holder 3 has a gripping element 30 which narrows over a conical region and merges into a hollow cylinder 32. This hollow cylinder 32 is chosen such that the sample receiving vessel 2 can be inserted into it. On the outer side of the hollow cylinder 32, leaf springs 33 are disposed which extend in the axial direction of the hollow tube 32. These leaf springs engage through the hollow tube 32 at recesses (grooves) 35 and, with the free end here, press on a rubber O-ring 34 which is disposed within the wall of the hollow tube 32.

If a sample receiving vessel 2 is introduced into the hollow cylinder 32 (FIG. 6C), then the leaf springs 33 press via the O-ring 34 on the sample receiving vessel 2 and hold it securely in its position. Hence the sample receiving vessel 2 is fixed in the holder 3.

If a sample is intended to be removed from the bioreactor 4, then the sample receiving vessel 2 is firstly inserted into the holder 3. The holder 3 is then introduced into the sample probe 1, the leaf springs 33 situated on the holder 3 being squeezed. They consequently exert an even greater pressure on the sample receiving vessel 2 in the sample probe 1. Upon further introduction of the holder 3 into the sample probe 1, the valve-side hollow needle 13 pierces the septum 21. By means of farther pressure on the holder 3 and hence on the sample receiving vessel 2, the spring 125 is compressed and the valve cylinder 18 is moved downwards. Hence the sealing ring 122 is then removed from its sealed seat and the openings 127 in the valve cylinder 18 are exposed. Hence the valve in the sample probe 1 is opened and the sample is conveyed by the pressure difference between the sample receiving vessel 2 and the interior of the reactor 4 into the sample receiving vessel 2 until there is pressure equalisation.

If the sample receiving vessel 2 is removed again from the sample probe 1 by pulling on the gripping element 30 of the holder 3, then the valve in the sample probe 1 is closed firstly by the spring force of the spring 124 and subsequently the sample receiving vessel 2 is pushed out of the sample probe 1 with assistance from the spring 125, the connection between the hollow needle 13 and the septum 21 being separated. The septum 21 then closes again.

Outwith the sample probe 1, the leaf springs 33 of the holder 3 still exert only a slight pressure on the sample receiving vessel 2 so that the now filled sample receiving vessel 2 can be removed easily from the holder 3.

The sample can then be used for further processing, in particular it can be centrifuged off directly in the sample receiving vessel 2 when using a suitable centrifuge insert.

FIG. 7 shows a particular embodiment of the holder 3 and of the sample probe 1 with which contamination of the bioreactor can be reliably precluded in a simple manner. The sample probe 1 is hereby provided with a groove 16. This groove is introduced into the inner wall of the sample probe 1 as a stepped groove 16. It has a first step 19*a* and also an end stop 19*b*. A pin 37 which is disposed on the holder 3 can be introduced into this groove 16. If the pin 37 is now introduced into the groove 16, then firstly a guided axial movement of the holder 3 is effected. Upon reaching the step 19*a*, the holder 3 must then be rotated in order to guide the pin subsequently further along the groove in order then to implement again an axial movement of the holder 3 up to the stop 19*b* at the end of the groove 16.

If the sampling system is now to be kept sterile between the samplings, then the holder 3 is fitted with a sample receiving vessel 2 which is filled with disinfectant. The holder 3 is thereby introduced only so far into the sample probe 1 that the pin 37 is situated in the step 19*a* of the groove 16. In this position, the needle 13 already penetrates through the septum 21 so that the needle is already disinfected or sterilised by the disinfectant contained in the sample receiving vessel 2. The valve of the sample probe 1 in this state is however closed, as is represented for example in FIG. 5A.

In the case where a sample is intended to be taken, the disinfectant vessel is removed and the holder is fitted with a suitable sample receiving vessel 2. Said holder is then introduced again into the sample probe 1, an axial movement of the pin in the groove 16 being implemented first and subsequently a lateral movement of the pin 37 in the groove 16 along the shoulder 19*a* and subsequently again an axial movement of the pin 37 in the groove 16 up to the stop 19*b*. In the latter position, the needle 13 pierces the septum 21 of the sample receiving vessel 2 and the valve cylinder 18 is displaced, as represented in FIG. 5B, in order to open the valve 12.

Hence the sample can flow into the sample receiving vessel 2.

As a result of the bayonet-type closure of the holder 3 in the sample probe 1, it is ensured that the different positions of the sample receiving vessels 2 can be adjusted safely and reliably for the different functions even by only slightly trained personnel.

FIG. 8 shows a sampling system according to the invention in which the sample receiving vessel 2 is retained on the holder 3 by means of a retaining clip 41. The right partial image shows the holder 3 with the retaining clip 41 outwith the sample probe 1 and the left partial image shows the same system introduced into the sample probe 1. The retaining clip 41 has a cylindrical basic body 42 with slot-like milled parts 43 in the sides of the receiving hole 44 for the sample vessel 2.

Figure 10:
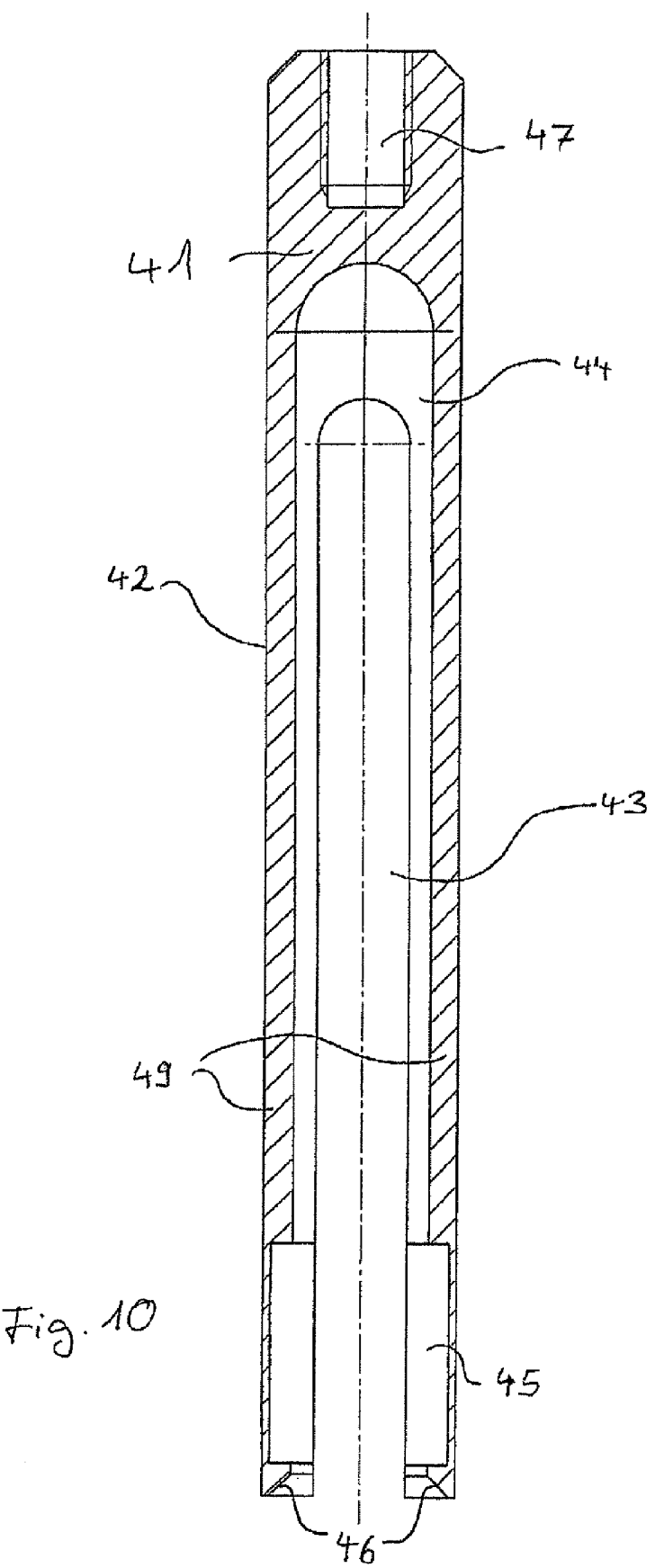
FIG. 10 shows the section through a retaining clip according to the invention.

FIG. 10 shows, enlarged, the section through such a retaining clip 41. The boring 44 is provided with a corresponding undercut 45 for receiving the cap 22 of the sample vessel 2. A corresponding sample vessel 2 is shown in FIG. 9. For easier introduction of the sample vessel 2 into the receiving hole 44, chamfers 46 are provided at the receiving opening. The mounting of the retaining clip 41 on the holder 3 can be effected via a threaded hole 47. If now a sample is intended to be taken from a bioreactor, then a sample vessel 2 with the spherical end 48 is inserted in advance in the retaining clip 41. The two halves 49 of the retaining clip 41 are thereby pushed apart until the cap 22 of the sample vessel 2 locks in the undercut. In this state, the two halves 49 of the clip 41 are pressed outwards slightly conically, only by introduction into the probe 1 is the cap 22 of the vessel 2 compressed again and does the clip 41 assume a cylindrical shape. Since the clip halves 42 in the probe 1 cannot yield in the radial direction, the vessel is retained securely in the clip 41 and sliding out is prevented. For removing the sample vessel 2, the two clip halves 49 must be bent up slightly manually, as a result of which the sample vessel 2 can be removed easily.

Figure 12:
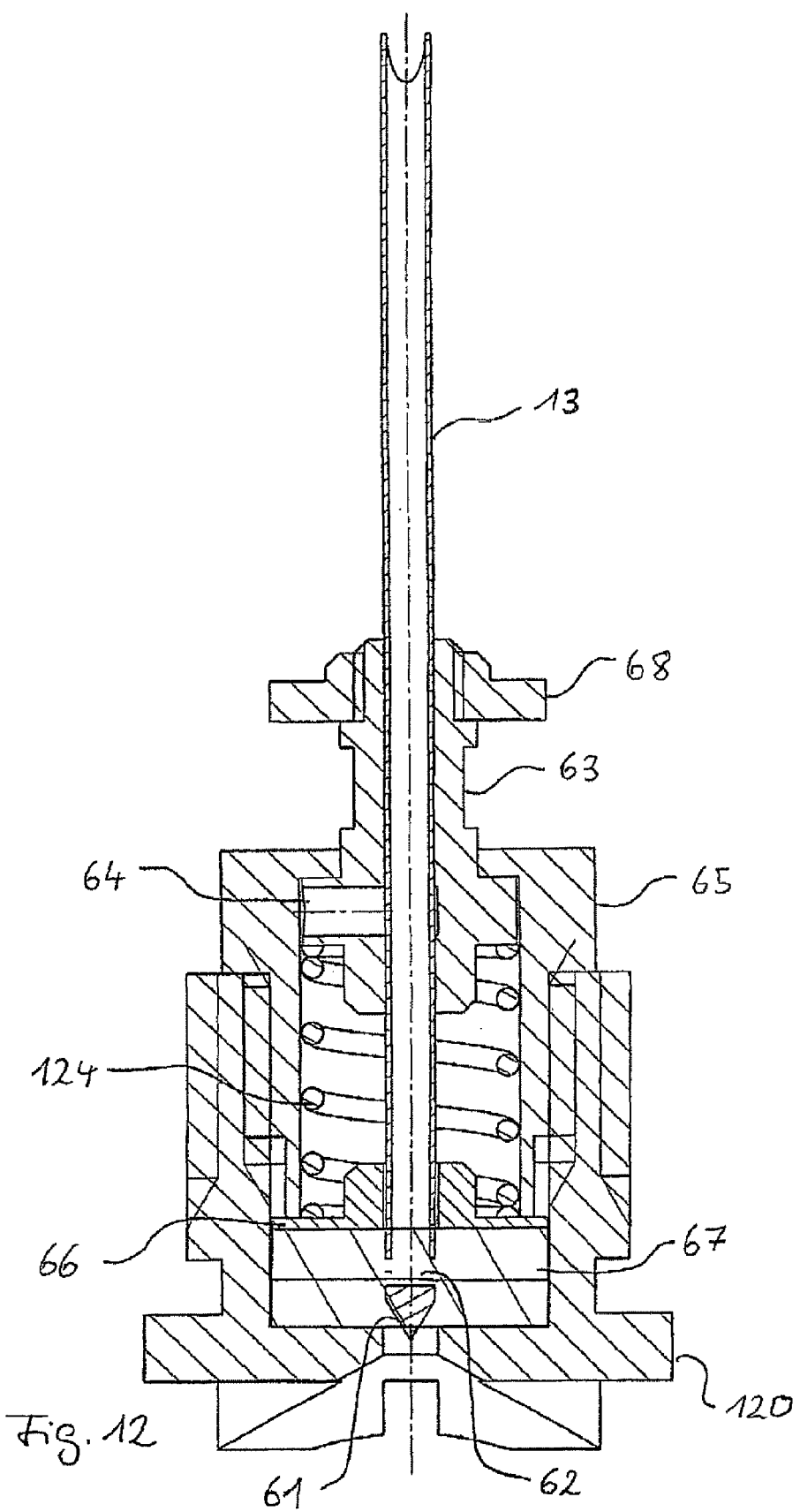
FIG. 12 shows the section through a valve according to the invention with a needle tip accommodated in a septum.
Figure 13:
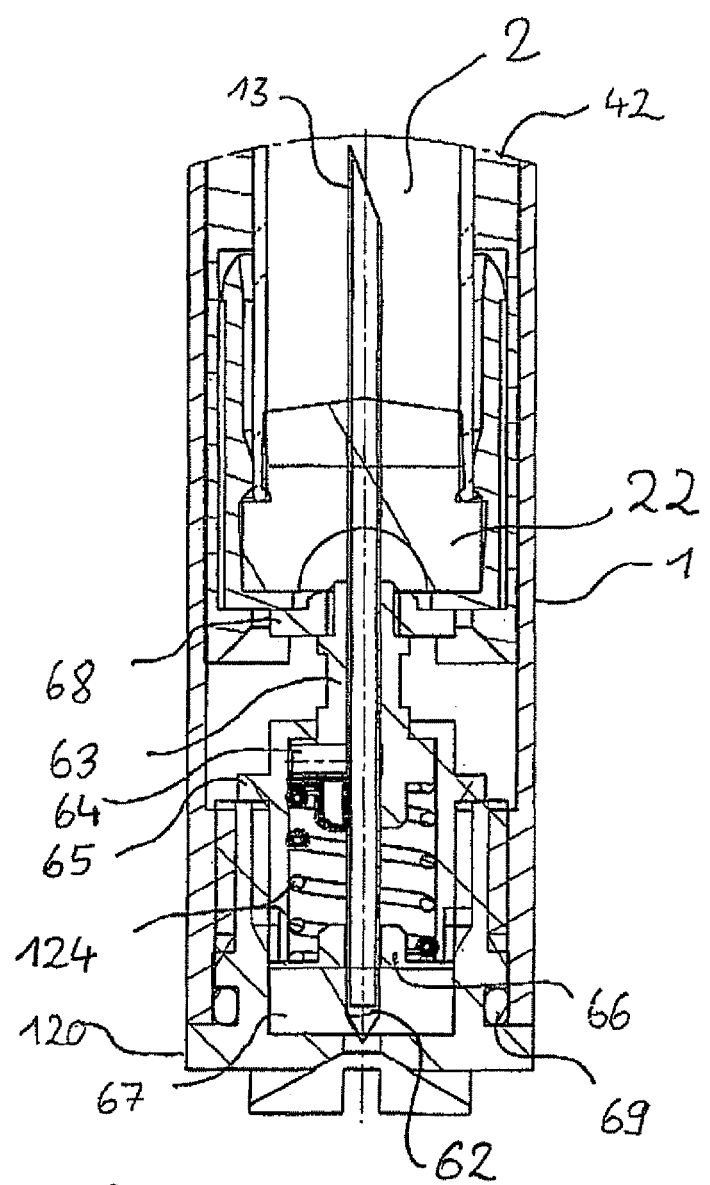
FIG. 13 shows a valve corresponding to FIG. 12 which is accommodated in a sampling probe.
Figure 14:
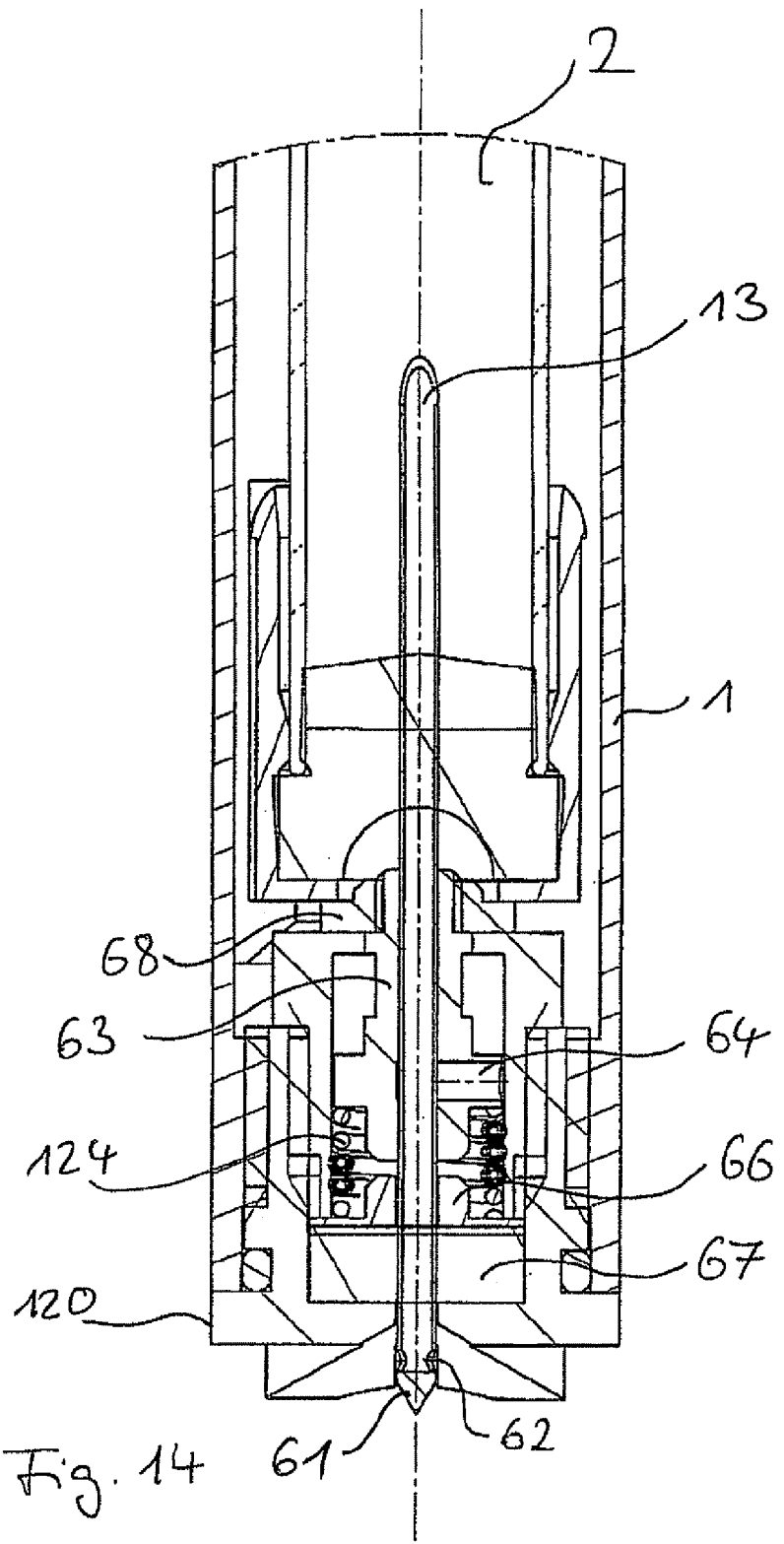
FIG. 14 shows a valve corresponding to FIG. 12 which is accommodated in a sampling probe and situated in the open state.

FIGS. 11, 12, 13 and 14 show an embodiment of the valve 12 according to the invention. In FIG. 11, an outer view of the valve can be seen, FIG. 12 shows a section through the valve according to the invention and FIGS. 13 and 14 shows the valve according to the invention when it is incorporated in the sampling probe 1 and connected to a sampling vessel 2. FIG. 13 hereby represents the closed state and FIG. 14 the opened state of the valve. Mounting of this valve is affected in that the canula 13 is arc welded on at one end; subsequently a tip 61 is ground and is provided with a cross-hole 62 just above the tip. The canula 13 is soldered into the needle body 63. For this purpose, a boring 64 is situated in the needle body 63 for introducing the solder. The catch 65 is screwed into the basic body 120 up to the stop and pretensions the spring 124 towards the pressure plate 66 and the septum 67 via the needle body. Subsequently, the stop 68 can be screwed onto the needle body 63. The mounted valve 12 is screwed into the tube 1 of the sampling probe from the bottom and sealed with an O-ring 69.

As can be detected in FIG. 13, the spring 124, in the closed state, presses the canula 13 via the needle body 63 in the direction of the sample vessel 2 and hence holds the cross-hole 62 in the septum 67. As a result of the pretension of the septum 67 by the catch 65, the septum 67 seals the cross-hole 62 of the needle 13 reliably. A sample vessel 2 introduced into the sampling probe 1 can be pressed onto the needle 13 in opposition to a slight resistance until the cap 22 of the vessel 2 is situated on the stop 60. A clear pressure point can thereby be felt. The pretension of the spring 124 prevents opening of the valve 12. Sealing of the needle cross-hole 62 by the septum 67 produces the vacuum in the sampling vessel 2.

As can be detected in FIG. 14, by increasing the pressure in opposition to the pressure spring 124, the needle tip 61 is pushed out of the septum 67 until reaching a second pressure point, as a result of which it is situated freely in the medium which is to be suctioned in. As a result, a continuous connection between the reactor interior and the sample vessel interior 2 is created and a sample can be suctioned into the sampling vessel 2 by means of the vacuum. By reducing the pressure on the valve 12, the spring 124 draws the canula 13 back into the septum 67 and hence closes the valve 12. The sampling vessel 2 can subsequently be withdrawn from the needle 13 in opposition to a slight resistance.

Figure 15:
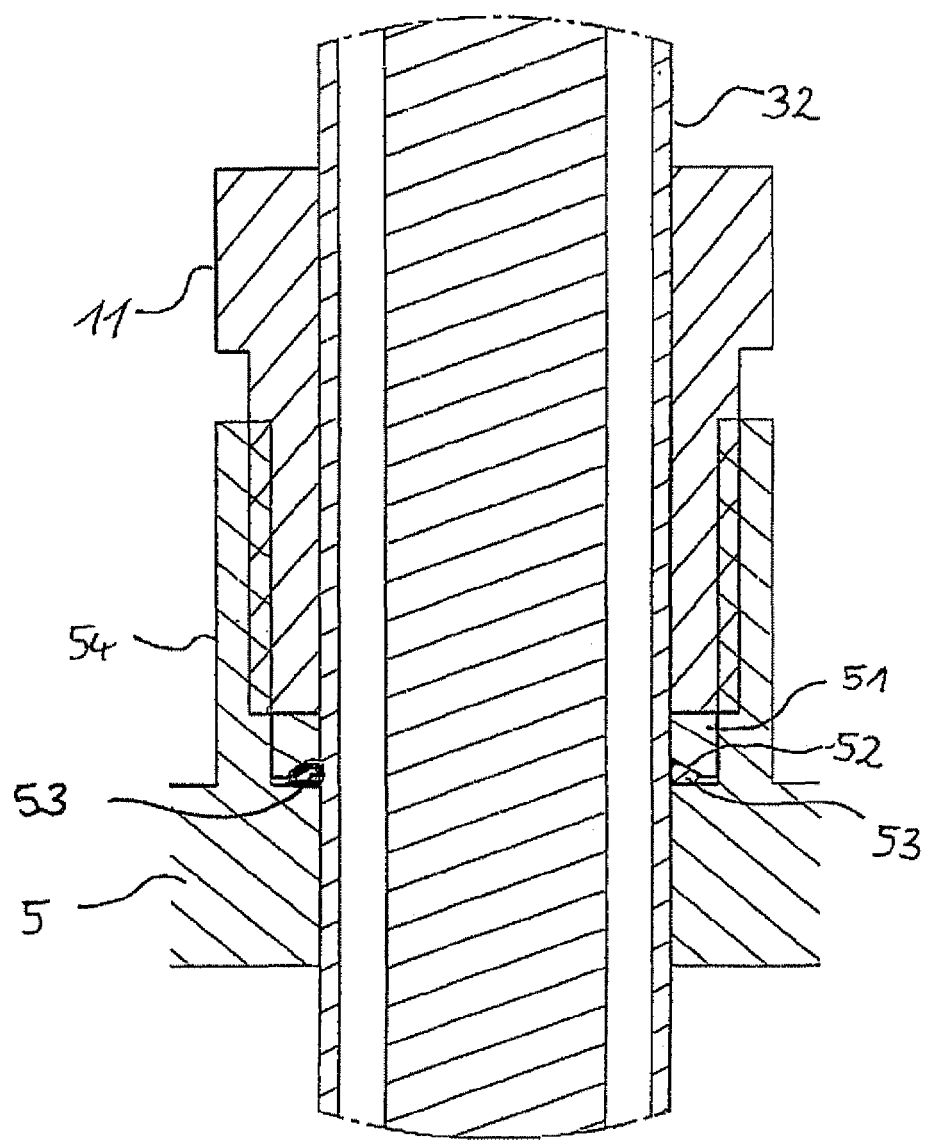
FIG. 15 shows a sealing screw connection of the sampling probe according to the invention.

FIG. 15 shows the possibility of a sealing cover screw connection. A ring 51 is hereby shrunk onto the tube 32 of the sampling probe 1. Said ring has an internally situated chamfer 52. An O-ring 53 is placed in the latter. With the help of the union nut 11, the O-ring 53 is pressed against the screw-in cup 54 and consequently forms a seal against the tube 32 and the cover 5. By using a shrunk-on ring 51, sampling probes 1 of different lengths can be manufactured very easily in production.

In summary, it can be established that, in contrast to previously implemented manual sampling with a dip pipe, in the case of the present invention, the dead volume can be reduced to a few μl directly in the reactor due to the sampling position. This is relevant in particular for laboratory reactors made of glass which are only accessible from the top. In addition, the practical implementation of a sampling operation is simplified greatly with the system according to the invention. Hence manual errors which occur frequently in the normal sampling operation according to the state of the art are avoided, so that the sampling operation can be implemented more reliably, more reproducibly and more safely.

The invention claimed is:

1. Sampling system for fluid samples comprising:
   a sample receiving vessel for receiving the sample, which is sealed by a septum;
   a holder for the sample receiving vessel configured to receive and hold the sample receiving vessel; and
   a sample probe for dipping into a fluid volume and for taking a fluid sample from the fluid volume,
   the sample probe being configured as a hollow volume which, at one end, has a first opening for introducing the holder and the sample receiving vessel and, at another end, is sealed by a first valve which is provided with a hollow needle which projects into an interior of the sample probe, said valve being able to be opened by contact with at least one of the group comprising the holder and the sample receiving vessel and then connecting an exterior of the sample probe to an inner volume of the hollow needle.

2. Sampling system according to claim 1, wherein the sample probe, the holder and the sample receiving system are configured cylindrically.

3. Sampling system according to claim 1, wherein the first opening of the sample probe has a mounting element configured to mount on a reactor.

4. Sampling system according to claim 1, wherein the sample receiving vessel is filled partially with a reagent.

5. Sampling system according to claim 1, wherein an interior of the sample receiving vessel has a lower pressure than the fluid volume.

6. Sampling system according to claim 1, wherein a spring is disposed in the sample probe and exerts a retroactive force on one or both of an introduced sample receiving vessel and an introduced holder.

7. Sampling system according to claim 1, wherein the sample receiving vessel is an at least partially evacuated test tube.

8. Sampling system according to claim 1, wherein the holder has a holding element which is configured as a hollow tube with an internal diameter which is greater than an external diameter of the sample receiving vessel.

9. Sampling system according to claim 8, wherein at least one spring element is disposed on the holding element and engages via a recess in a wall of the hollow tube in an interior of the hollow tube.

10. Sampling system according to claim 9, wherein the spring element is a leaf spring.

11. Sampling system according to claim 10, wherein the leaf spring has a first end which is disposed securely on an outside of the hollow tube and a second free end, the second free end engaging at least partially into the recess.

12. Sampling system according to claim 9, wherein a sealing ring is disposed in a region of the recess in the wall of the hollow tube or within the hollow tube.

13. Sampling system according to claim 1, wherein the holder is cylindrical in a region which receives the sample receiving vessel, wherein an edge of the region which receives the sample receiving vessel being cut into along at least one part of its length on opposite sides.

14. Sampling system according to claim 1, wherein the samples probe and the holder have complementary stop elements which fix predetermined penetration depths of the holder into the sample probe.

15. Sampling system according to claim 1, wherein the holder has a pin and the sample probe, on an inner side thereof, has a stepped groove for engagement and for guidance of the pin, the stepped groove having, in an axial direction of the sample probe, at least a first step and a second stop, and wherein upon abutment of the pin against the first step, the septum of the sample receiving vessel is situated in the holder being pierced by the hollow needle and, upon abutment against the second stop, the valve is opened in addition.

16. Sampling system according to claim 1, wherein the sample probe, on an inner side thereof, has a pin and the holder has a stepped groove for engagement and for guidance of the pin, the groove having, in an axial direction of the holder, at least a first step and a second stop, wherein upon abutment of the pin against the first step, the septum of a sample receiving vessel is situated in the holder being pierced by the hollow needle and, upon abutment against the second stop, the valve is opened in addition.

17. Use of a sampling system according to claim 1, for sampling from laboratory reactors, bioreactors, reactors made of glass, for taking toxic or health-endangering samples from reactors and/or for removing liquids or gases.

18. Sampling system according to claim 1, wherein a part of the sample receiving vessel which is not filled with liquid is evacuated at least partially.

* * * * *